(12) United States Patent
Nielsen

(10) Patent No.: US 9,102,462 B2
(45) Date of Patent: Aug. 11, 2015

(54) NICOTINE-CONTAINING CHEWING GUM PIECE PACKED IN A WRAPPING OF LAMINATE

(75) Inventor: Kaj Hovhave Nielsen, Vejle Ost (DK)

(73) Assignee: Fertin PHARMA A/S, Vejle Ost (DK)

( * ) Notice: Subject to any disclaimer, the term of this patent is extended or adjusted under 35 U.S.C. 154(b) by 0 days.

(21) Appl. No.: 13/542,291

(22) Filed: Jul. 5, 2012

(65) Prior Publication Data

US 2013/0011461 A1 Jan. 10, 2013

(30) Foreign Application Priority Data

Jul. 6, 2011 (DK) .................................. 2011-70369

(51) Int. Cl.
| | | |
|---|---|---|
| *B65D 85/60* | (2006.01) | |
| *A61K 9/68* | (2006.01) | |
| *B65D 75/12* | (2006.01) | |
| *A23G 4/06* | (2006.01) | |

(Continued)

(52) U.S. Cl.
CPC *B65D 85/60* (2013.01); *A23G 4/06* (2013.01); *A23G 4/068* (2013.01); *A61K 9/0058* (2013.01); *B29C 65/02* (2013.01); *B29C 66/1122* (2013.01); *B29C 66/133* (2013.01); *B29C 66/4312* (2013.01); *B29C 66/4322* (2013.01); *B29C 66/72321* (2013.01); *B29C 66/83413* (2013.01); *B29C 66/849* (2013.01); *B32B 15/085* (2013.01); *B32B 15/09* (2013.01); *B32B 15/20* (2013.01); *B32B 27/06* (2013.01); *B32B 27/32* (2013.01); *B32B 27/36* (2013.01); *B65B 9/06* (2013.01); *B65B 51/16* (2013.01); *B65B 51/30* (2013.01); *B65D 75/12* (2013.01); *B65D 75/14* (2013.01); *B29C 65/08* (2013.01); *B29C 65/085* (2013.01); *B29C 65/18* (2013.01); *B29C 66/71* (2013.01); *B29C 66/72328* (2013.01); *B29C 66/7352* (2013.01); *B29C 2795/002* (2013.01); *B32B 2307/31* (2013.01); *B32B 2553/00* (2013.01)

(58) Field of Classification Search
CPC ...... B65D 85/60; B65D 75/12; A61K 9/0058; A23G 4/06; B29C 65/02; B65B 51/16
See application file for complete search history.

(56) References Cited

U.S. PATENT DOCUMENTS

| | | | |
|---|---|---|---|
| 4,908,027 A | 3/1990 | Enscore et al. | |
| 2008/0170814 A1* | 7/2008 | Bowers et al. | ................ 383/204 |

FOREIGN PATENT DOCUMENTS

| | | |
|---|---|---|
| BE | 1010444 A5 | 8/1998 |
| EP | 0 480 127 A1 | 4/1992 |

(Continued)

OTHER PUBLICATIONS

Ribbon Mic Material, 2011 (last comment 2009), Gearslutz.com, pp. 1-18.*

*Primary Examiner* — Trevor Love
(74) *Attorney, Agent, or Firm* — Sughrue Mion, PLLC

(57) ABSTRACT

A nicotine-containing chewing gum piece packed in a wrapping of laminate, where the laminate comprises at least an inner layer facing the chewing gum and a nicotine degradation agent barrier layer of a metal foil. The nicotine-containing chewing gum piece is shaped as an elongate plate having two ends and a thickness and a length, where the length is in the range of 8 to 20 times the thickness. The wrapping has two elongate edges sealed to one another in a fin area extending along the length of the chewing gum piece and two sealed end areas extending beyond the ends of the chewing gum piece.

19 Claims, 4 Drawing Sheets

(51) Int. Cl.
*B29C 65/02* (2006.01)
*B65B 51/16* (2006.01)
*B65D 75/14* (2006.01)
*B29C 65/00* (2006.01)
*B65B 51/30* (2006.01)
*B65B 9/06* (2012.01)
*B32B 15/085* (2006.01)
*B32B 15/09* (2006.01)
*B32B 15/20* (2006.01)
*B32B 27/06* (2006.01)
*B32B 27/32* (2006.01)
*B32B 27/36* (2006.01)
*B29C 65/08* (2006.01)
*B29C 65/18* (2006.01)

(56) References Cited

FOREIGN PATENT DOCUMENTS

| | | | |
|---|---|---|---|
| GB | 2 393 392 A | 3/2004 | |
| GB | 2 423 757 A | 9/2006 | |
| WO | 91/09731 A1 | 7/1991 | |
| WO | WO95/25436 * | 9/1995 | ............... A23G 3/30 |
| WO | 96/14763 A1 | 5/1996 | |
| WO | 01/83326 A1 | 11/2001 | |
| WO | 2007/024891 A2 | 3/2007 | |
| WO | WO2007/100720 * | 9/2007 | |
| WO | 2009/115160 A2 | 9/2009 | |

\* cited by examiner

NICOTINE-CONTAINING CHEWING GUM PIECE PACKED IN A WRAPPING OF LAMINATE

CROSS-REFERENCE TO RELATED APPLICATIONS

The present application claims the benefit of priority from Danish Patent Application No. PA 2011 70369 filed on Jul. 6, 2011.

STATEMENT REGARDING FEDERALLY SPONSORED RESEARCH OR DEVELOPMENT

Not Applicable

REFERENCE TO A MICROFICHE APPENDIX

Not Applicable

BACKGROUND OF THE INVENTION

The present invention relates to a nicotine-containing chewing gum piece packed in a wrapping of laminate.

A nicotine-containing chewing gum piece packed in a wrapping of laminate is known from blister packs, where the laminate comprises a back sheath and a front foil, typically of transparent material. Examples of blister packed nicotine-containing chewing gums are described in GB-A 2 423 757, where several sheaths are contained in an outer packet, or in WO 2007/024891, where the blister pack is enclosed in an outer member. The individual chewing gum piece is oval shaped in cross-section, a classical shape used for coated chewing gum pieces having a length of about 19 mm, a width of about 12 mm, and a maximum thickness of about 5 mm.

Nicotine-containing chewing gum is typically manufactured in this classical pellet shape, which is suitable for the coating process. Nicotine-containing chewing gum pieces can be manufactured in ball-shape, which minimizes the surface area for a given amount of chewing gum mass. Nicotine-containing chewing gums are coated either by a sweetener or by polished wax. The reason for this is that the coating or wax polish is considered necessary to provide a barrier on the outside of the chewing gum material containing the nicotine. Nicotine is a very volatile substance at room temperature, and it is a very well known problem for nicotine-containing chewing gum that nicotine evaporates from the gum material in the period from manufacture to consumption. In order to provide an acceptable shelf-life it has been considered mandatory to retard evaporation of nicotine from the gum material by on the one hand manufacturing the chewing gum piece in a shape having a small outer surface in relation to the mass of chewing gum, and on the other hand providing the chewing gum piece with the coating or wax polish that retards evaporation.

Despite these efforts, nicotine actually does evaporate from the nicotine-containing chewing gum piece prior to it being sold to the consumer. Nicotine-containing chewing gum is blister-packed, and the common blister packing has a transparent foil layer extending over the chewing gum piece to one side of the package. After shelf-storing for about half a year of wax polished nicotine-containing chewing gum it is not uncommon to observe a brownish layer on the inside of the transparent foil layer, and this brownish layer is deposited, degraded nicotine evaporated off from the chewing gum piece. In order to minimize this adverse effect and minimize the extent to which nicotine degrades into reaction products, in particular under the influence of oxygen, nicotine-containing chewing gum is normally manufactured with a hard-coating enclosing the chewing gum material. It is also known to stabilize nicotine with a cation exchange resin, such as Amberlite®. In has thus been accepted to have a loss of up to 5% of the nicotine contained in the chewing gum piece, which loss is caused by both evaporation and degradation of the nicotine prior to consumption by the user.

In addition to the problem of nicotine evaporation, nicotine-containing chewing gums are also sensible to degradation of nicotine due to influences from oxygen, moisture and light. WO 91/09731 describes packing of transdermal delivery devices for the transport of nicotine base across the skin, and in order to alleviate the problem of nicotine degradation during storage it is suggested to use a laminate having a nicotine degradation agent barrier layer in form of a metal foil, such as a foil of aluminium. According to WO 91/09731 the inner layer of the laminate must be a nicotine barrier layer, more specifically a layer of nitrile rubber modified acrylonitrile-methyl acrylate copolymer. Transdermal delivery devices for the transport of nicotine base across the skin are patches to be placed on the skin during use. Such patches typically have a low ability to retain nicotine enclosed in the patch material, at least when compared with chewing gum, which is a more stable carrier for nicotine, because nicotine is typically carried in gum base, which in itself present a barrier to nicotine evaporation.

BRIEF SUMMARY OF THE INVENTION

Blister packing of nicotine-containing chewing gums may provide advantages in sealing the individual gum piece off from the surroundings and thus advantages in respect of avoiding degradation of the nicotine due to influences of oxygen, moisture and light, but the blister packing used for nicotine-containing chewing gums poses a problem to the consumers.

Consumers of nicotine-containing chewing gums are previous smokers who have decided to quit smoking. They typically associate smoking with social activity, and they often tend to be particularly tempted to use nicotine when in social surroundings. One example is the social activity following a dinner where the temptation to smoke may be pronounced. In this situation, discomfort is easily felt when nicotine-containing chewing gum is used instead of smoking. The blister-packed chewing gums are quite noisy to press out of the blister packing, and blister packing involves a sensation of medication. The blister packing of nicotine-containing chewing gums are thus easily providing the consumer with an anti-social feeling, because sickness is not a social-improving signal. This may cause a problem to former smokers needing the nicotine effect of the chewing gum when in public, social surroundings.

It is an aim of the present invention to provide a nicotine-containing chewing gum piece packed in a wrapping of laminate that eliminates this adverse effect on the former smoker.

According to the present invention the initially mentioned nicotine-containing chewing gum piece is packed in a wrapping of laminate, wherein the laminate comprises a nicotine degradation agent barrier layer of a metal foil, wherein the nicotine-containing chewing gum piece is shaped as an elongate plate having two ends and a thickness (t) and a length (l), where the length is in the range of 5 to 20 times the thickness (5×t≤l≤20×t), and wherein the wrapping of laminate is sealed in edge areas.

The shaping of the nicotine-containing chewing gum piece as an elongate plate provides the chewing gum piece with an appearance of a traditionally stick-shaped chewing gum known for about 100 years as a chewing gum used for pleasure. The shape of the chewing gum piece provides the piece with a very large surface area in relation to the chewing gum mass, and this runs counter to the desire to minimize evaporation of nicotine from the gum mass. This adverse effect of the shape, an effect particular to nicotine-containing chewing gum pieces, is surprisingly acceptable in view of the advantages it provides to the consumer.

Not only is the nicotine-containing chewing gum piece packed in a wrapping of laminate packed and shaped in a manner that avoids resembling medicaments and sickness, but opening of the package can be performed without producing the characteristic noise from a blister packed product. The sealed areas can be opened and the nicotine-containing chewing gum piece be removed from the wrapping rather silently.

The sealing of the wrapping of laminate in the edge areas encloses the nicotine-containing chewing gum piece completely within the laminate so that oxygen and light is prevented from accessing the interior containing the nicotine-containing chewing gum piece.

An additional advantage is provided in that the headspace—the void filled with air—in between the wrapping and the outer surface of the nicotine-containing chewing gum piece is much smaller that the headspace present in a blister packing. The reduced headspace counteracts the negative influences of the larger surface area of the chewing gum piece present with the plate-shaped piece in relation to the hitherto used oval-shaped piece for nicotine-containing chewing gum pieces.

In an embodiment the wrapping has two elongate edge areas sealed to one another in a fin area extending along the length of the chewing gum piece and two sealed end areas extending beyond the ends of the chewing gum piece. The wrapping of the chewing gum piece in the laminate having two elongate edge areas sealed to one another in a fin area extending along the length of the chewing gum piece and two sealed end areas extending beyond the ends of the chewing gum piece provides on the one hand an effective sealing of the chewing gum piece within the wrapping, and on the other hand it provides the consumer with a wrapping that can easily be opened.

Although it may be possible to coat the nicotine-containing chewing gum piece in order to minimize evaporation of nicotine, it is in an embodiment possible that the nicotine-containing chewing gum piece is uncoated. In view of producing the chewing gum piece it is an advantage that it is uncoated, as coating of a plate-shaped chewing gum piece requires a manufacturing process where the coating is sprayed onto the plate-shaped piece, and this involves higher manufacturing costs. To the consumer it is an advantage that the chewing gum piece is uncoated, because it then resembles traditional chewing gum in stick-shape.

In an embodiment according to the present invention the sealing of the fin area and of the two sealed end areas is a cold sealing. The cold sealing provides the advantage of closing the wrapping in a sealing manner without subjecting the chewing gum material to the influence of heat, an influence that would tend to degrade the nicotine content in the chewing gum material. Cold sealing may be provided by an inner layer of the laminate being self-adherent and sealing when pressure is provided to both sides of the laminate layers in the fin area and in the end areas. Such pressure may be provided on the outside of the laminate after the insides of opposed laminate layers have been brought into mutual contact. As an alternative, the sealing may be provided by applying heat to the joining areas, but this is not preferred because of the risk of degrading the chewing gum material located close to the area being sealed.

In a further development of this embodiment the sealing of the fin area and of the two sealed end areas is an ultrasonic welding sealing. Ultrasonic welding provides several advantages, first of all the advantage that only very little heat is dissipated into the laminate during the sealing process. Another advantage, which can be useful to sealing of the elongated edge areas in a fin area, is the possibility of using roller contact weld heads on the opposed sides of the laminate in the fin area.

In another further development of the embodiment the sealing of the fin area and of the two sealed end areas is an ultrasonic welding sealing comprising at least two parallel weld zones in each area. The additional weld zone or weld zones improve the sealing effect of the welding and can be easily accomplished by providing the weld heads with several, spaced apart, protruding contact areas.

In an embodiment the nicotine degradation agent barrier layer is an aluminium foil. An advantage of using an aluminium foil resides in that it provides an effective barrier to oxygen as it is available in qualities having few pinholes, and it is readily available on the market. The aluminium foil can have a thickness of about 8 µm. This thickness on the one hand provides an efficient barrier for oxygen and light access to the inner of the laminated packing, and thus protects the nicotine contained in the chewing gum from degrading, and on the other hand the aluminium foil has such a limited thickness that the enveloping of the chewing gum piece may be effected at high speed and with a laminate which readily adapts its shape to the contour of the plate-shaped chewing gum piece, because the laminate has such a limited thickness that it can be folded in shape to tightly follow the outer surface of the chewing gum piece, which promotes a reduction of the headspace around the plate-shaped chewing gum piece. In another embodiment the aluminium foil has a thickness of about 12 µm. This thickness improves the long term barrier effect of the aluminium foil in particular with regard to oxygen diffusion through the barrier layer. This thickness may be useful if the nicotine-containing chewing gum piece packed in a wrapping of laminate must have a long shelf-life.

In a further embodiment the aluminium foil has a thickness in the range of 8 µm to 20 µm, such as a thickness in the range from 11 µm to 20 µm. If the thickness of the aluminium foil exceeds 20 µm, the laminate has less ability to tightly follow the contour of the plate-shaped gum piece, and as a result an undesired increase in the volume of the headspace occurs. The thickness of about 11 µm provides the laminate with an effective oxygen diffusion barrier, and at the same time the laminate is readily folded or bent to follow the shape of the nicotine-containing chewing gum piece.

It is possible to utilize the nicotine degradation agent barrier layer as an outer layer of the packed nicotine-containing chewing gum piece. However, a polyethylene terephthalate (PET) layer can also be provided as an outer layer on the laminate, as this provides an appealing outer surface which is not looking like a medicament package.

The PET layer may be provided as it is, but the appealing appearance of the product may be further distinguished from a medicament package in that a printed layer is provided on the inside of the polyethylene terepthalate (PET) layer. Such a printed layer may comprise any desired graphics and thus signalise leisure and consumption of a leisure product.

The inner layer of the laminate may be a layer as described in the above-mentioned international application WO 91/09731, but it is preferably an inner layer of a thermoplastic polymer, preferably a polyethylene or a cross-linked polyethylene (PEX). Thermoplastic polymers are well suited for bonding together in an effective sealing in a cold process or with using a minimum of dissipated heath during a welding process. This facilitates the manufacturing process and enables the packaging to be performed at an advantageously high speed in a cost-effective process.

Nicotine-containing chewing gum pieces have typically been manufactured with a content of gum base in the range from 65% to 70%. It is possible to use such a gum base content also with the nicotine-containing chewing gum pieces according to the present invention, however advantages are obtainable in manufacturing the nicotine-containing chewing gum pieces with a content of from 30% to 50% gum base. This lower content of gum base makes the chewing gum pieces softer and more easy to bite into in the initial chew, and when packed in a wrapping having a fin area extending along the length of the plate-shaped gum piece, it becomes easier to open the wrapping in a peel away manner where the gum piece is bent during the process. If the gum base content is reduced below 30% it may exhibit a tendency for it to break apart when bent. If the gum base content exceeds 50% then the gum mass remaining in the mouth during prolonged chewing may be considered larger than liked by most consumers. Chewing of the gum piece is improved when the nicotine-containing chewing gum pieces are softer, and this is in particular an advantage to consumers having a high need for nicotine stimulation.

In a further embodiment the nicotine-containing chewing gum piece contains in the range from 1 mg to 5 mg nicotine, such as in the range from 2 mg to 4 mg nicotine.

In an embodiment the nicotine-containing chewing gum piece has a weight of about 2 g. This weight is larger than the weight of the prior art coated chewing gum pieces, but is considered acceptable for the gum pieces according to the present invention, as a piece having a weight of about 2 g is able to satisfy a consumer in the need for feeling a sufficient mass of chewing gum in the mouth, just by chewing a single piece of the nicotine-containing chewing gum. The weight of the chewing gum piece may be larger than 2 g, but it may also be smaller than 2 g. The chewing gum piece can e.g. have a weight of about 1.5 g or about 1.6 g or about 1.7 g, such as a weight in the range from 1.5 g to 1.7 g.

BRIEF DESCRIPTION OF THE SEVERAL VIEWS OF THE DRAWING

Examples of the invention will now be explained below with reference to the very schematical drawings, in which.

DETAILED DESCRIPTION OF THE INVENTION

Figure 1:
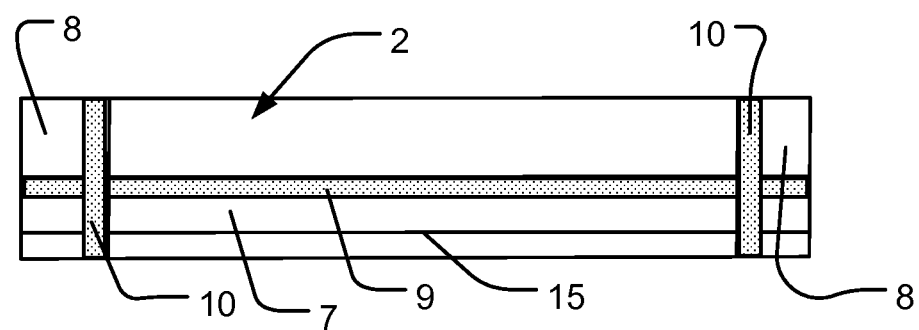
FIG. 1 depicts a view from above of a nicotine-containing chewing gum piece in a wrapping of laminate according to the present invention.
Figure 3:
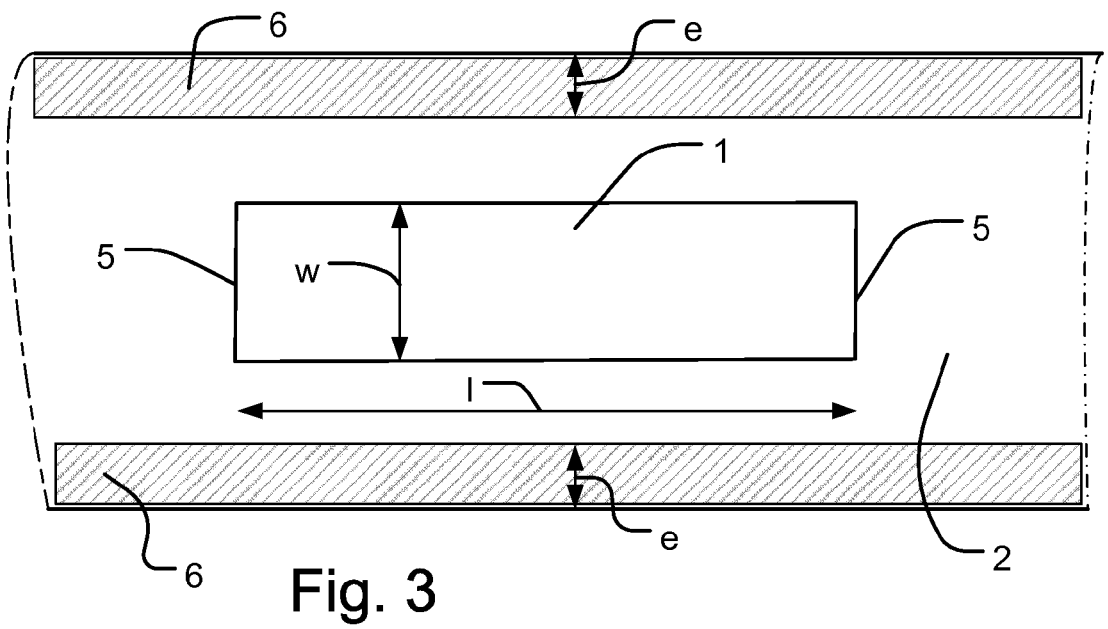
Figure 4:
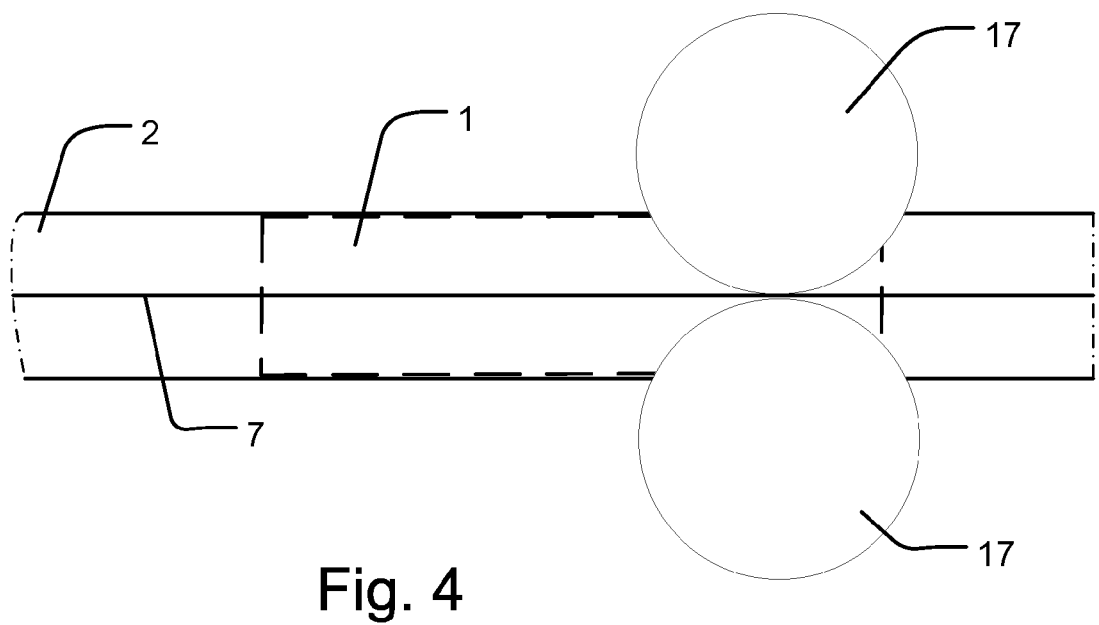
Figure 5:
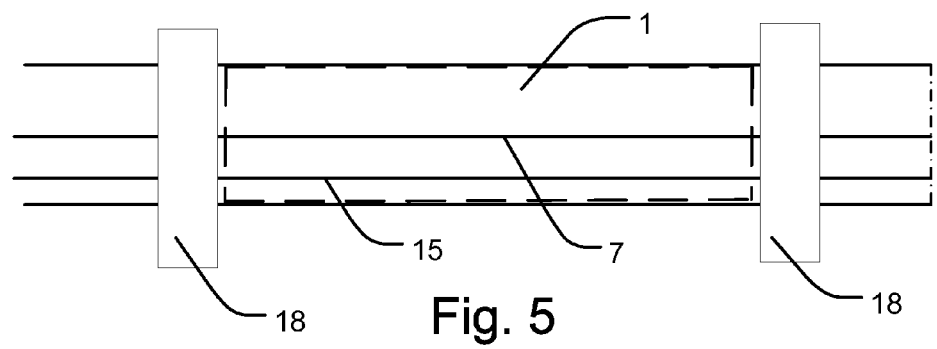

A nicotine-containing chewing gum piece 1 is illustrated in FIG. 3 placed on a wrapping of laminate 2, and in FIG. 1 the wrapping around the chewing gum piece has been completed. The chewing gum piece is shaped as an elongate plate and has a certain length l between its two ends 5, a certain width w (FIG. 3) and a certain thickness t (FIG. 1). As illustrated in FIG. 1 the wrapping of laminate 2 completely encloses the chewing gum and extends beyond ends 5 of the plate-shaped chewing gum piece in two end areas 8. The wrapping of laminate has at either of its two longitudinal edges an elongate edge area 6, which edge area has been illustrated with shading in FIG. 3. Edge area 6 has a width e of such a size that the inner width of the wrapping in between edge areas 6 substantially corresponds to $2 \times (w+t)$. The inner width may have a slight oversize in comparison to the circumferential length $2 \times (w+t)$ of the chewing gum piece in the transverse direction in order to allow the laminate to bend in a curved manner at the corners of the chewing gum piece. The chewing gum piece may have parallel opposed sides.

The wrapping of laminate has been folded around the longitudinal edges of the nicotine-containing chewing gum piece 1 and the end areas 6 have been folded back and placed against one another and sealed to one another, thus forming a fin area 7 standing up from the nicotine-containing chewing gum piece 1. The fin area has been folded down towards the flat side of the wrapped gum piece and then the two end areas 8 have been sealed next to the ends 5 of the plate shaped chewing gum piece.

The resulting wrapping of laminate has a longitudinal sealing 9 in the fin area 7 and a sealing 10 of each end area 8. The individual sealing 10 is preferably located close to the associated end 5 of the chewing gum piece, as is illustrated in FIG. 1. The fin area 7 has an outer longitudinal edge 15, which in the folded down position of the fin area is located to one lateral side of the upper side of the wrapped chewing gum piece.

Figure 2:
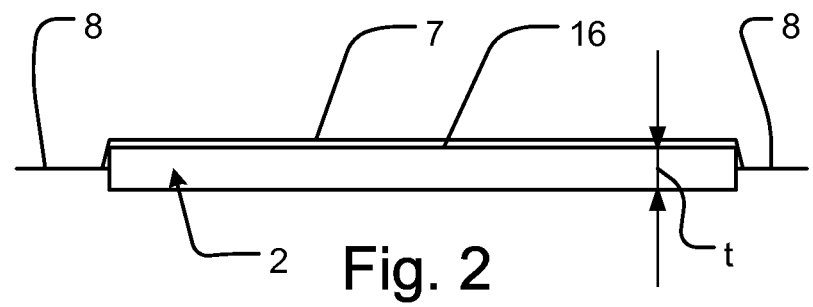
FIG. 2 depicts a side view of the gum piece in the wrapping of FIG. 1, FIGS. 3-5 illustrate in views from above an example of how to place the wrapping around the chewing gum piece of FIG. 1, and FIGS. 6-8 illustrate a cross-section through illustrative examples of wrapping laminates for wrapping around the chewing gum piece of FIG. 1.

In FIG. 2 is illustrated that fin area 7 is located close to an upper side 16 of the laminate enclosing the chewing gum piece, and that the ends of fin area 7 are joined to the outer end areas 8 by the sealing 10 in either end area 8. Fin area 7 thus has longitudinal edge 15 lying a little distance away from the upper side 16 in a position, which is easy to grab with fingers.

The sealing 9 of the fin area and/or the sealing 10 of one or the other end area are preferably made with such a sealing strength that a child cannot easily break the seal. This sealing strength can be provided in various manners. The strength can e.g. be provided by a strong bonding between the sealed, abutting laminate layers, or the strength can be provide with a weaker bonding covering a larger area. The larger area can be provided by increasing the width of the sealing. The larger width is also an advantage in view of isolating the interior of the wrapping from the ambient atmosphere. On the other hand, senior people may be consumers of the nicotine-containing chewing gum piece, and in this case the wrapping of laminate should be sufficiently easy to break open to allow the required manipulation to be performed even with hands weakened by age. In order to allow this, and yet provide a sufficient child-guarding effect, the mentioned high sealing strength may be combined with additional features that facilitate opening, such a tear away ribbon, notches in edge areas, or weakened fold lines.

The nicotine-containing chewing gum piece is shaped as an elongate plate and may have different dimensions. The following Table 1 provides non-exhaustive examples:

TABLE 1

| Length l | Thickness t | Width w |
| --- | --- | --- |
| 45 mm | 3 mm | 12 mm |
| 35 mm | 5 mm | 10 mm |

TABLE 1-continued

| Length l | Thickness t | Width w |
| --- | --- | --- |
| 47 mm | 3 mm | 12 mm |
| 45 mm | 3 mm | 10 mm |
| 22 mm | 4 mm | 16 mm |
| 20 mm | 4 mm | 24 mm |
| 30 mm | 6 mm | 9 mm |
| 40 mm | 2 mm | 16 mm |

Other dimensions are of cause possible. The thickness is preferably substantially constant in the individual nicotine-containing chewing gum piece.

An example of providing the chewing gum piece 1 with a wrapping of laminate is described in the following. The chewing gum piece 1 is placed on top of a laminate as illustrated in FIG. 3, and the laminate is folded around the longitudinal edges of the piece towards the middle of the piece. The two longitudinal edge areas 6 are folded upwards and away from the longitudinal centre line of the chewing gum piece and are brought into mutual abutment with the insides of edge areas 6 in contact with one another. Then the edge areas upstanding from the chewing gum piece are moved in between rotating wheels of a first welding unit 17 and a sealing 9 is provided. The sealing may be provided by the wheels of the first welding unit being pressed together on opposite sides of the edge areas 6, possibly under supersonic welding influence from the first welding unit 17 or under addition of heat to the wheels. The sealing is preferably located in vicinity of the chewing gum piece. The sealing 9 provided by first welding unit 17 creates the fin area. In a subsequent process, following a folding of the fin area to be in contact with the upper side 16 of the wrapping, a second welding unit 18 extending transversely across the band of laminate provides the sealing 10 in the end area in front of the chewing gum piece and in the opposed end area behind the chewing gum piece. The three sealing thus provides a complete sealing of all edge areas of the wrapping of laminate. Following this, the laminate is cut in the transverse direction in front of and behind the chewing gum piece, or at least at one on the ends if the other end already has the desired length from a cut performed for a previous chewing gum piece. The second welding unit 18 may also perform the sealing under supersonic welding influence, or under addition of heat.

Welding units 17 and 18 are well-known in the art of lamination. The welding may be effected as ultrasonic welding, which has the advantage of dissipating only very little heat to the laminate, or it may be heat welding. If the inner layer 3 is of a self-sealing material, the sealing 10 at either end and the sealing 9 may be made by pressing the laminate layers together, and in this case pressure rolls can be used instead of welding units.

As an alternative to making the sealing as a single sealing, one or more of the sealing 10 at either end and the sealing 9 can be made as two or more, such as three, four, five or more, sealings extending in parallel in a spaced apart pattern.

Figure 6:
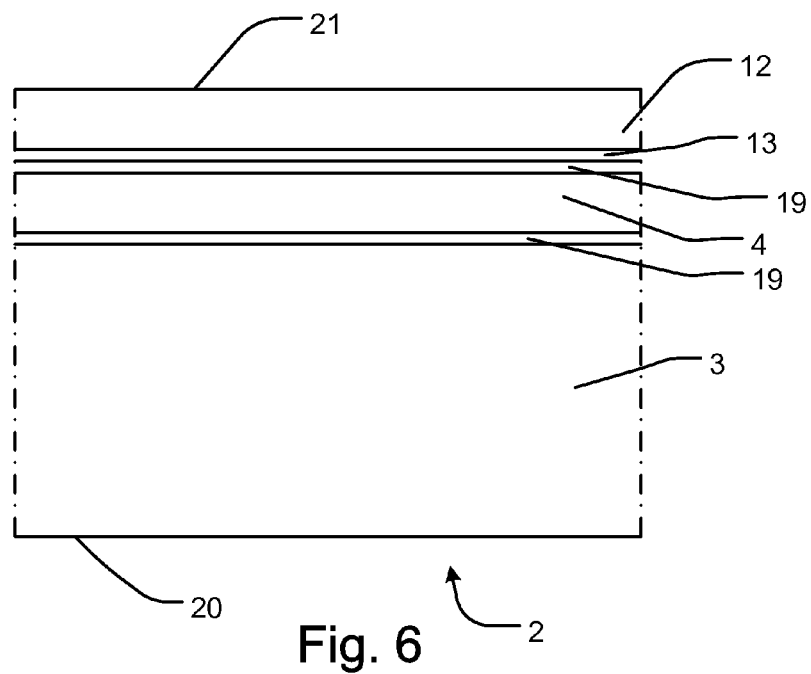

The wrapping of laminate may in one example illustrated in FIG. 6 comprise an outer layer 12 of polyethylene terepthalate (PET) in a layer thickness of 12 µm, a printed layer 13 provided either by printing on the inside of outer layer 12 prior to performing the lamination or by providing a paper layer with print, which paper layer is integrated in the lamination process. A bonding layer 19, such as a layer of adhesive, attaches an aluminium layer 4 acting as a nicotine degradation agent barrier layer. The aluminium foil layer 4 has thickness of about 8 µm, and on the inside of layer 4 there is another bonding layer 19 fixing an inner layer 3 to the inside of the aluminium layer 4. Inner layer 3 is a layer of polyethylene in a layer thickness of 40 µm.

Figure 7:
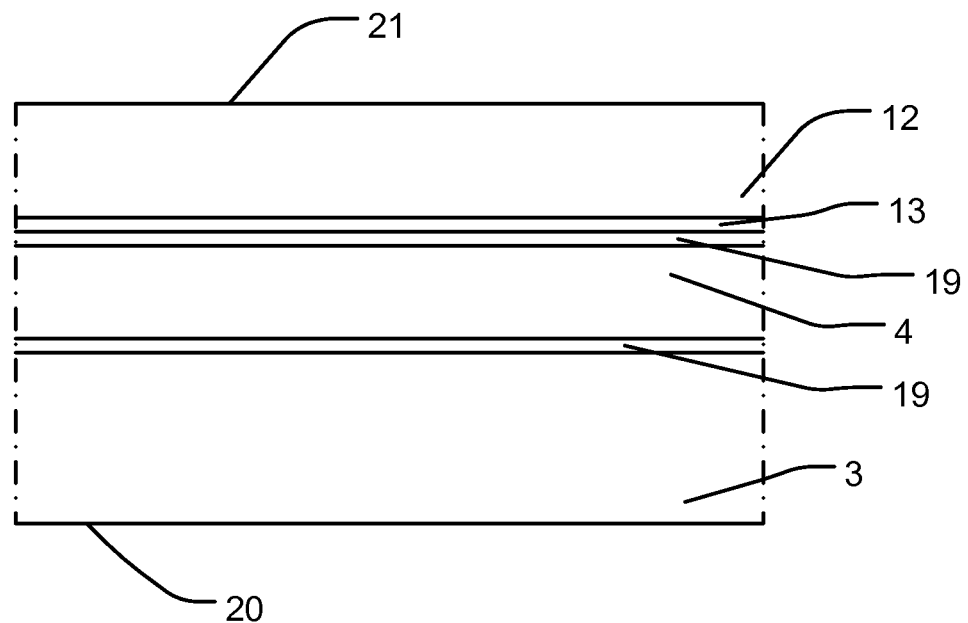

The wrapping of laminate may in an example illustrated in FIG. 7 comprise an outer layer 12 of polyethylene terepthalate (PET) in a layer thickness of 23 µm, a printed layer 13 provided either by printing on the inside of outer layer 12 prior to performing the lamination or by providing a paper layer with print. A bonding layer 19, such as a layer of adhesive, attaches an aluminium layer 4 acting as a nicotine degradation agent barrier layer. The aluminium foil layer 4 has thickness of about 12 µm, and on the inside of layer 4 there is another bonding layer 19 fixing an inner layer 3 to the inside of the aluminium layer 4. Inner layer 3 is a layer of cross-linked polyethylene in a layer thickness of 20 µm.

Figure 8:
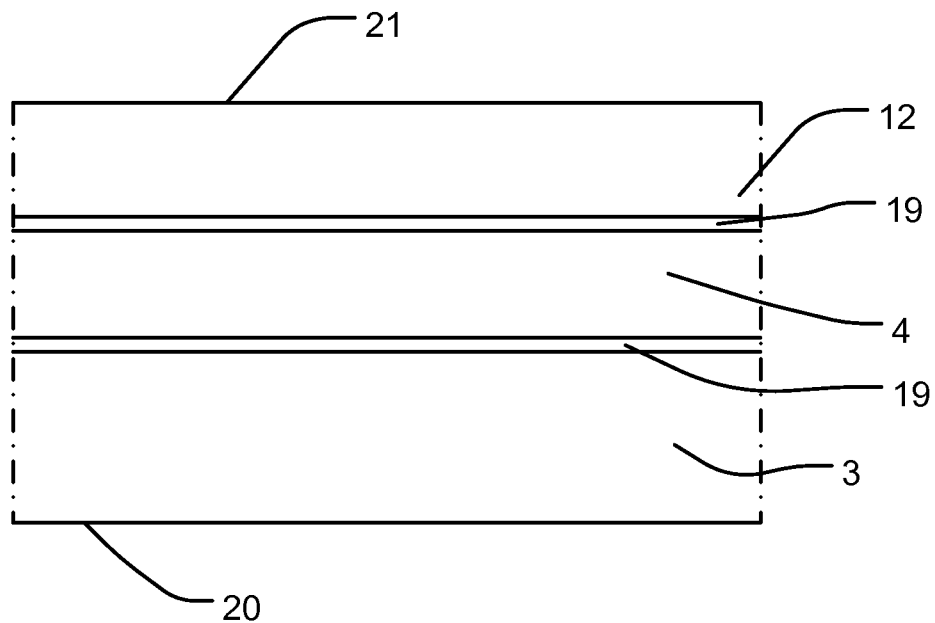

The wrapping of laminate may furthermore as illustrated in FIG. 8 be without a printed layer, in which case the outer layer is bonded directly to the aluminium layer 4. In the above examples bonding layers are provided for assembling the laminate. Such bonding layers are well known in the art of manufacturing laminates and they are typically of an adhesive applied to the aluminium foil or to the inside of the outer layer 12 or on top of the inc printed onto the inside of the outer layer or to inner layer 3 during the lamination process. As an example the adhesive may be a bi-component polyurethane adhesive, or another commercial grade of adhesive. As an alternative to using an adhesive bonding layer, the aluminium layer 4 can be provided directly onto the surface of the inner layer 3 or directly onto the surface of the outer layer 12. In this case, the binding between the aluminium layer and the plastic layer can be made by extrusion bonding where a hot plastic, such as polyethylene, is deposited from an extrusion die located at a combining roll nip, formed by a rubber and a steel roll. The steel roll is chilled to affect the bond by setting or solidifying the plastic quickly onto the aluminium surface. The combined aluminium and plastic foil is thus used in the subsequent lamination process for manufacturing the wrapping of laminate.

It is also possible to make inner layer 3 or outer layer 12 of other polymeric materials than PET, PE or PEX, such as polypropylene PP or a acrylonitrile-methyl acrylate copolymer. The metal foil layer may be of other metals than aluminium, such as copper or another metal or alloy, which provides a nicotine degradation agent barrier layer. The nicotine degradation agents are typically oxygen, light and possibly moisture. The nicotine degradation agent barrier layer provides a layer that is substantially free of pinholes or has such a low degree of pinholes that oxygen passage is significantly reduced or hindered during the typical shelf life of the nicotine-containing chewing gum piece, such as during a period of 6 months or a year.

The individual layers of the laminate may be modified to have other thicknesses than described in the above. The metal foil layer may e.g. have a thickness of 14 µm, or 17 µm or possibly 20 µm. Also the outer layer 12 and the inner layer 3 may have other thicknesses than described in the above, as is well known from the art of laminating wrappings.

The wrapping of laminate may enclose the nicotine-containing chewing gum piece in other manners than the manner where the wrapping has two elongate edge areas sealed to one another in a fin area extending along the length of the chewing gum piece and two sealed end areas extending beyond the ends of the chewing gum piece. In one alternative wrapping the nicotine-containing chewing gum piece 1 has been placed on the laminate a short distance away from one of the longitudinal edges of the laminate, such as the distance e from the edge or even closer to the edge. The opposite longitudinal edge of the laminate has then been lifted up and folded in over the top of the chewing gum piece and positioned with the inside of the laminate in contact with the portion of the laminate edge area extending beyond the piece 1. At least portions of the two longitudinal edge areas 6 are thus in mutual abutment and are brought into contact with a sealing device which provides a sealing or several parallel sealings in the longitudinal direction of the piece 1. The sealing device may provide a flat seal or may be adapted to roll or fold the portions of the two longitudinal edge areas into bulge-shape during the sealing process. It the latter case a ridge or bulge of roundish cross-section extends along the longitudinal edge of the wrapped nicotine-containing chewing gum piece 1. The end areas 8 have been sealed in the manner as described in the above. It is likewise possible to cut the wrapping of laminate before sealings 10 are made, and then roll or fold the end portions into bulge-shape during the sealing process. It the latter case a ridge or bulge of roundish cross-section extends along the ends 5 of piece 1.

The nicotine-containing chewing gum piece 1 may have a composition of well-known type, but preferably is contains from 30% to 50% gum base and the major components of the remaining 70% to 50% being sorbitol powder and filler supplemented with traditional chewing gum components like flavour, intense sweetener etc. The nicotine-containing chewing gum piece contains in the range from 1 mg to 5 mg nicotine, preferably in the range from 2 mg to 4 mg nicotine. As explained in the above an ion exchange resin is preferably also present in the composition in an amount suitable for stabilizing the nicotine.

A more specific example of the nicotine-containing chewing gum piece 1 is described in the following.

EXAMPLE 1

Preparation of Gum Base

A gum base was prepared, which comprised the following ingredients.

| Ingredients | % by weight |
|---|---|
| Elastomer | 10 |
| Natural resin | 28 |
| Synthetic resin | 22 |
| Fat/wax/emulsifiers | 23 |
| Fillers | 17 |

The elastomer and filler were added to a mixing kettle provided with mixing means like e.g. horizontally placed Z-shaped arms. The kettle had been preheated for 15 minutes to a temperature of about 120° C. The rubber was sheared and grinded with mechanical action in the kettle.

Resin was slowly added to the elastomer and filler until the mixture became homogeneous. The remaining resin was then added to the kettle and mixed for 10-20 minutes. The softening ingredients were added and mixed for 20-40 minutes until the whole mixture became homogeneous.

The mixture was then discharged into the pan and allowed to cool to room temperature from the discharged temperature of 120° C.

EXAMPLE 2

Preparation of Nicotine-Containing Chewing Gum

Chewing gum was prepared by use of the gum base in Example 1 and according to a conventional mechanical mixing procedure during moderate use of heating as described below. There were prepared five different compositions CG1 to CG5 as set out in Table 2.

TABLE 2

|  | CG1 | CG2 | CG3 | CG4 | CG5 |
|---|---|---|---|---|---|
| Gum base | 43.4% | 43.4% | 43.4% | 43.4% | 43.4% |
| Filler | 14.6% | 14.6% | 14.6% | 14.6% | 14.6% |
| Nicotine Polacrilex |  |  |  |  |  |
| Nicotine | 0.2% | 0.2% | 0.2% | 0.2% | 0.2% |
| Ion exchange resin | 0.8% | 0.8% | 0.8% | 0.8% | 0.8% |
| Buffer agents |  |  |  |  |  |
| Sodium hydrogen carbonate | 1.0% | 1.0% | 1.0% | 1.0% | 1.0% |
| Sodium carbonate | 2.0% | 2.0% | 2.0% | 2.0% | 2.0% |
| C8-triglycerides | 0.0% | 1.3% | 2.6% | 5.2% | 7.8% |
| C10-triglycerides | 0.0% | 0.7% | 1.4% | 2.8% | 4.2% |
| Sorbitol powder | 34.6% | 31.4% | 30.6% | 26.6% | 22.6% |
| Glycerin | 0.0% | 1.2% | 0.0% | 0.0% | 0.0% |
| Intense sweetener | 0.4% | 0.4% | 0.4% | 0.4% | 0.4% |
| Flavor | 3.0% | 3.0% | 3.0% | 3.0% | 3.0% |

Gum base and filler were mixed batch-wise in a mixing kettle provided with mixing means like e.g. horizontally placed Z-shaped arms. The kettle had been preheated to a temperature of up to approximately 50° C. When the content was homogenous the other ingredients were added. Nicotine was added in the first half of the mixing process. Finally, after mixing, chewing gums were formed through extrusion and rolling into plate-shaped chewing gum pieces.

The pieces, in uncoated condition, were then ready for being provided with a wrapping of laminate in the manner described in the above with reference to FIG. 3.

Alternatively, the mixing step may be performed continuously in a conventional extruder process, partly or fully replacing the mixing involving the Z-blade mixer.

The nicotine added may be in form of pure nicotine, of a nicotine salt or nicotine bound to an ion exchange resin, e.g. Amberlite IRP 64. It is emphasized that several other gum base compositions may be applied within the scope of the present invention.

The nicotine-containing chewing gum pieces may be formulated with 0.1 mg to 8 mg of nicotine per piece, preferably 2 or 4 mg.

It is possible to dust the pieces with talcum or another anti-tack agent if this promotes the handling of the pieces.

The above-mentioned embodiments may be modified within the scope of the patent claims, and features from the individual embodiments described may be combined into further embodiments within the scope of the patent claims.

The invention claimed is:

1. A nicotine-containing chewing gum piece packed in a wrapping of laminate, the laminate comprising at least an inner layer facing the chewing gum, wherein the laminate comprises a nicotine degradation agent barrier layer of a metal foil; the nicotine-containing chewing gum piece is shaped as an elongate plate having two ends and a thickness (t) and a length (l), where the length is in the range of 5 to 20 times the thickness ($5 \times t \leq l \leq 20 \times t$), and wherein the wrapping of laminate is sealed in edge areas;

wherein the chewing gum piece is made of a single layer, the single layer having gum base and nicotine mixed throughout, wherein the chewing gum is not hard coated such that the single layer is also an exterior layer of the chewing gum piece prior to being packed in the wrapping of laminate, wherein the nicotine-containing chewing gum piece contains from 30% to 70% gum base,
wherein the nicotine-containing chewing gum piece contains in the range from 1 mg to 8 mg nicotine, and
wherein the single layer is homogenous throughout.

2. A nicotine-containing chewing gum piece packed in a wrapping of laminate according to claim 1, wherein the wrapping has two elongate edge areas sealed to one another in a fin area extending along the length of the chewing gum piece and two sealed end areas extending beyond the ends of the chewing gum piece.

3. A nicotine-containing chewing gum piece packed in a wrapping of laminate according to claim 2, wherein the sealing of the fin area and of the two sealed end areas is a cold sealing.

4. A nicotine-containing chewing gum piece packed in a wrapping of laminate according to claim 3, wherein the sealing of the fin area and of the two sealed end areas is an ultrasonic welding sealing.

5. A nicotine-containing chewing gum piece packed in a wrapping of laminate according to claim 3, wherein the sealing of the fin area and of the two sealed end areas is an ultrasonic welding sealing comprising at least two parallel weld zones in each area.

6. A nicotine-containing chewing gum piece packed in a wrapping of laminate according to claim 1, wherein the nicotine degradation agent barrier layer is an aluminum foil.

7. A nicotine-containing chewing gum piece packed in a wrapping of laminate according to claim 6, wherein the aluminum foil has a thickness of about 8 µm or of about 12 µm.

8. A nicotine-containing chewing gum piece packed in a wrapping of laminate according to claim 6, wherein the aluminum foil has a thickness in the range of 8 µm to 20 µm.

9. A nicotine-containing chewing gum piece packed in a wrapping of laminate according to claim 1, wherein a polyethylene terepthalate (PET) layer is provided as an outer layer on the laminate.

10. A nicotine-containing chewing gum piece packed in a wrapping of laminate according to claim 9, wherein a printed layer is provided on the inside of the polyethylene terepthalate (PET) layer.

11. A nicotine-containing chewing gum piece packed in a wrapping of laminate according to claim 1, wherein the inner layer is of a thermoplastic polymer, selected from a polyethylene or a cross-linked polyethylene (PEX).

12. A nicotine-containing chewing gum piece packed in a wrapping of laminate according to claim 2, wherein the nicotine-containing chewing gum piece contains from 30% to 50% gum base.

13. A nicotine-containing chewing gum piece packed in a wrapping of laminate according to claim 12, wherein the nicotine-containing chewing gum piece contains in the range from 1 mg to 5 mg nicotine.

14. A nicotine-containing chewing gum piece packed in a wrapping of laminate according to claim 1, wherein the nicotine-containing chewing gum piece has a weight of about 2 g.

15. A nicotine-containing chewing gum piece packed in a wrapping of laminate according to claim 6, wherein the aluminum foil has a thickness in the range of 11 µm to 20 µm.

16. A nicotine-containing chewing gum piece packed in a wrapping of laminate according to claim 12, wherein the nicotine-containing chewing gum piece contains in the range from 2 mg to 4 mg nicotine.

17. A nicotine-containing chewing gum piece packed in a wrapping of laminate, the laminate comprising at least an inner layer facing the chewing gum, wherein the laminate comprises a nicotine degradation agent barrier layer of a metal foil; the nicotine-containing chewing gum piece is shaped as an elongate plate having two ends and a thickness (t) and a length (l), where the length is in the range of 5 to 20 times the thickness ($5 \times t \leq l \leq 20 \times t$), and wherein the wrapping of laminate is sealed in edge areas;
wherein the chewing gum piece is made of a single layer, the single layer having gum base and nicotine mixed throughout,
wherein the chewing gum is not hard coated such that the single layer is also an exterior layer of the chewing gum piece prior to being packed in the wrapping of laminate,
wherein the nicotine-containing chewing gum piece contains from 30-50% gum base,
wherein the nicotine-containing chewing gum piece contains in the range from 1 mg to 8 mg nicotine, and
wherein the single layer is homogenous throughout.

18. A nicotine-containing chewing gum piece packed in a wrapping of laminate, the laminate comprising at least an inner layer facing the chewing gum, wherein the laminate comprises a nicotine degradation agent barrier layer of a metal foil; the nicotine-containing chewing gum piece is shaped as an elongate plate having two ends and a thickness (t) and a length (l), where the length is in the range of 5 to 20 times the thickness ($5 \times t \leq l \leq 20 \times t$), and wherein the wrapping of laminate is sealed in edge areas;
wherein the chewing gum piece is made of a single layer, the single layer having gum base and nicotine mixed throughout,
wherein the chewing gum is not hard coated such that the single layer is also an exterior layer of the chewing gum piece prior to being packed in the wrapping of laminate,
wherein the nicotine-containing chewing gum piece contains from 30% to 70% gum base,
wherein the nicotine-containing chewing gum piece contains in the range from 2-4 mg nicotine, and
wherein the single layer is homogenous throughout.

19. A nicotine-containing chewing gum piece packed in a wrapping of laminate, the laminate comprising at least an inner layer facing the chewing gum, wherein the laminate comprises a nicotine degradation agent barrier layer of a metal foil; the nicotine-containing chewing gum piece is shaped as an elongate plate having two ends and a thickness (t) and a length (l), where the length is in the range of 5 to 20 times the thickness ($5 \times t \leq l \leq 20 \times t$), and
wherein the wrapping of laminate is sealed in edge areas;
wherein the chewing gum piece is made of a single layer, the single layer having gum base and nicotine mixed throughout,
wherein the chewing gum is not hard coated such that the single layer is also an exterior layer of the chewing gum piece prior to being packed in the wrapping of laminate,
wherein the nicotine-containing chewing gum piece contains from 30% to 50% gum base,
wherein the nicotine-containing chewing gum piece contains in the range from 2-4 mg nicotine, and
wherein the single layer is homogenous throughout.

* * * * *